United States Patent [19]

Bedford et al.

[11] Patent Number: 5,972,603
[45] Date of Patent: Oct. 26, 1999

[54] DNA POLYMERASE WITH MODIFIED PROCESSIVITY

[75] Inventors: Ella Bedford, Brookline; Stanley Tabor, Cambridge; Charles C. Richardson, Chestnut Hill, all of Mass.

[73] Assignee: President and Fellows of Harvard College, Cambridge, Mass.

[21] Appl. No.: 08/656,555

[22] Filed: May 31, 1996

Related U.S. Application Data

[63] Continuation-in-part of application No. 08/599,224, Feb. 9, 1996, abandoned.
[51] Int. Cl.$^6$ .............................. C12Q 1/68; C12Q 1/70; C07K 1/00
[52] U.S. Cl. .................................. 435/6; 435/5; 530/350
[58] Field of Search ............................ 435/5, 6; 530/350

[56] References Cited

U.S. PATENT DOCUMENTS

| 4,795,699 | 1/1989 | Tabor | 435/5 |
| 5,466,591 | 11/1995 | Abramson et al. | 435/194 |
| 5,614,365 | 3/1997 | Tabor et al. | 435/6 |

OTHER PUBLICATIONS

Asakura et al., "Cloning, Nucleotide Sequence, and Expression in *Escherichia coli* of DNA Polymerase Gene (polA) from *Thermus thermophilus* HB8," *J. Ferment. Bioeng.* 76:265–269 (1993).
Ausubel et al., Current Protocols in Molecular Biology, Wiley Interscience, New York, 16.2.2 (1990).
Beese et al., "Structure of DNA Polymerase I Klenow Frament Bound to Duplex DNA," *Science* 260:352–355 (1993).
Blanco et al., "A general structure for DNA–dependent DNA polymerases," *Gene* 100:27–38 (1991).

Bryant et al., "Elementary Steps in the DNA Polymerase I Reaction Pathway," *Biochemistry* 22:3537–3551 (1983).
Chaiken et al., "Analysis of Macromolecular Interactions using Immobilized Ligands," *Analytical Biochemistry* 201:197–210 (1992).
Huber et al., "*Escherichia coli* Thioredoxin Stabilizes Complexes of Bacteriophage T7 DNA Polymerase and Primed Templates," *J. Biol. Chem.* 262:16224–16232 (1987).
Joyce and Grindley, "Construction of a plasmid that overproduces the large proteolytic fragment (Klenow fragment) of DNA polymerase I of *Escherichia coli*," *Proc. Natl. Acad. Sci. USA* 80:1830–1834 (1983).
Lopez et al., "Characterization of the polA Gene for *Streptococcus pneumoniae* and Compositions of the DNA Polymerase I It Encodes to Homologous Enzymes from *Escherichia coli* Phage T7," *J. Biol. Chem.* 264:4255–4263 (1989).
Lu et al., "Histidine Patch Thioredoxins," *J. Biol. Chem.* 271:5059–5065 (1996).
Malmqvist, "Biospecific Interaction Analysis Using Biosensor Technology," *Nature* 361:186–187 (1994).
Myers and Gelfand, "Reverse Transcription and DNA Amplification by a *Thermus thermophilus* DNA Polymerase," *Biochemistry* 30:7661–7666 (1991).
Sarkar et al., "The "Megaprimer" Method od Site–Directed Mutagenesis," *BioTechniques* 8(4):404–407 (1990).
Tabor and Richardson, "Selective Inactivation of the Exonuclease Activity of Bacteriophage T7 DNA Polymerse by in Vitro Mutagenesis," *J. Biol. Chem.* 264(11):6447–6458 (1989).
Yehle and Ganesau, "Deoxyribonucleic Acid Synthesis in Bacteriophage SP01–infected *Bacillus subtilis*," *J. Biol. Chem.* 248:7456–7463 (1973).

*Primary Examiner*—Ardin H. Marschel
*Assistant Examiner*—Jezia Riley
*Attorney, Agent, or Firm*—Lyon & Lyon LLP

[57] ABSTRACT

Chimeric DNA polymerase having a DNA polymerase domain and processivity factor binding domain not naturally associated with DNA polymerase domain.

14 Claims, 9 Drawing Sheets

```
GTGATTTCTTATGACAACTACGTCACCATCCTTGATGAAGAAACACTGAAAGCGTGGATTGCGAAGCTGGAA
AAAGCGCCGGTATTTGCATTTGATACCGAAACCGACAGCCTTGATAACATCTCTGCTAACCTGGTCGGGCTT
TCTTTTGCTATCGAGCCAGGCGTAGCGGCATATATTCCGGTTGCTCATGATTATCTTGATGCGCCCGATCAA
ATCTCTCGCGAGCGTGCACTCGAGTTGCTAAAACCGCTGCTGGAAGATGAAAAGGCGCTGAAGGTCGGGCAA
AACCTGAAATACGATCGCGGTATTCTGGCGAACTACGGCATTGAACTGCGTGGGATTGCGTTTGATACCATG
CTGGAGTCCTACATTCTCAATAGCGTTGCCGGGCGTCACGTATATGGACAGCCTCGCGGAACGTTGGTTGAAG
CACAAAACCATCACTTTTGAAGAGATTGCTGGTAAAGGCAAAAATCAACTGACCTTTAACCAGATTGCCCTC
GAAGAAGCCGGACGTTACGCCGCCGAAGATGCAGATGTCACCTTGCAGTTGCATCTGAAAATGTGGCCGGAT
CTGCAAAAACACAAAGGGCCGTTGAACGTCTTCGAGAATATCGAAATGCCGCTGGTGCCGGTGCTTTCACGC
ATTGAACGTAACGGTGTGAAGATCGATCCGAAAGTGCTGCACAATCATTCTGAAGAGCTCACCCTTCGTCTG
GCTGAGCTGGAAAAGAAAGCGACCGAAACGTTCGGCTCGTGGTATCAGCCTAAAGGTGGCACTGAGATGTTC
TGCCATCCGCGAACAGGTAAGCCACTACCTAAATACCCTCGCATTAAGACACCTAAAGTTGGTGGTATCTTT
AAGAAGCCTAAGAACAAGGCACAGCGAGAAGGCCGTGAGCCTTGCGAACTTGATACCCGCGAGTACGTTGCT
GGTGCTCCTTACACCCCAGTTGAACATGTTGTGTTTAACCTTTCTTCCACCAAGCAGTTACAAACCATTCTC
TTTGAAAAACAGGGCATTAAACCGCTGAAGAAAACGCCGGGTGGCGCGCCGTCAACGTCGGAAGAGGTACTG
GAAGAACTGGCGCTGGACTATCCGTTGCCAAAAGTGATTCTGGAGTATCGTGGTCGGCGAAGCTGAAATCG
ACCTACACCGACAAGCTGCCGCTGATGATCAACCCGAAAACCGGGCGTGTGCATACCTCTTATCACCAGGCA
GTAACTGCAACGGGACGTTTATCGTCAACCGATCCTAACCTGCAAAACATTCCGGTGCGTAACGAAGAAGGT
CGTCGTATCCGCCAGGCGTTTATTGCGCCAGAGGATTATGTGATTGTCTCAGCGGACTACTCGCAGATTGAA
CTGCGCATTATGGCGCATCTTTCGCGTGACAAAGGCTTGCTGACCGCATTCGCGGAAGGAAAAGATATCCAC
CGGGCAACGGCGGCAGAAGTGTTTGGTTTGCCACTGGAAACCGTCACCAGCGAGCAACGCCGTAGCGCGAAA
GCGATCAACTTTGGTCTGATTTATGGCATGAGTGCTTTCGGTCTGGCGCGGCAATTGAACATTCCACGTAAA
GAAGCGCAGAAGTACATGGACCTTTACTTCGAACGCTACCCTGGCGTGCTGGAGTATATGGAACGCACCCGT
GCTCAGGCGAAAGAGCAGGGCTACGTTGAAACGCTGdACGGACGCCGTCTGTATCTGCCGGATATCAAATCC
AGCAATGGTGCTCGTCGTGCAGCGGCTGAACGTGCAGCCATTAACGCGCCAATGCAGGGAACGCCGCCGAC
ATTATCAAACGGGCGATGATTGCCGTTGATGCGTGGTTACAGGCTGAGCAACCGCGTGTACGTATGATCATG
CAGGTACACGATGAACTGGTATTTGAAGTTCATAAAGATGATGTTGATGCCGTCGCGAAGCAGATTCATCAA
CTGATGGAAAACTGTACCCGTCTGGATGTGCCGTTGCTGGTGGAAGTGGGGAGTGGCGAAAACTGGGATCAG
GCGCACTAAGATTCGCCTGAACATGCCTTTTTTCGTAAGTAAGCAACATAAGCTGTCACGTTTTGTGATGGC
TATTAGAAATTCCTATGCAACAACTGAAAAAAAATTACAAAAAGTGCTTTCTGAACTGAACAAAAAAGAGTA
AAGTTAGTCGCGTAGGGTACAGAGGTAAGATGTTCTATCTTTCAGACCTTTTACTTCACGTAATCGGATTTG
GCTGAATATTTTAGCCGCCCCAGTCAGTAATGACTGGGGCGTTTTTTATTGGGCGAAAGAAAAGATCCGTAA
TGCCTGATGCGCTATGTTTATCAGGCCAACGGTAGAATTGTAATCTATTGAATTTACGGGCCGGATACGCCA
CATCCGGCACAAGCATTAAGGCAAGAAAATTATTCGCCGTCCTGCGTTTCTTCTACAGGCTGCATCTCGCTA
AACCAGGTATCCAGTTTCTGCCGCAGCTTGTCCACGCCTTGTTTCTTCAACGAAGAAAACGTTTCAACCTGC
ACATCACCGTTAAACGCCAGTACAGCTTCACGCACCATATTCAATTGCGCTTTACGTGCGCCGCTTGCCAGT
TTGTCCGCTTTGGTCAGCAGCACCAGAACGGCGATATTGCTGTCTAGCTTATCGATGATAAGCTGTCAAACA
TGAGAATTAAATCAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTGTAGATAACTACGA
TACGGGAGGGCTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGGTTCCCAACGATCAA
GGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGACCGAGTT
GCTCTTGCCCGGCGTCAACACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAACCCACTCGTG
CACCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATAAACAAATAGGGG
TTCCGCGCACATTTCCCCGAAAAGTGCCACCTCACGTCTAAGAAACCATTATTATCATGACATTAACCTATA
AAAATAGGCGTATCACGAGGCCCTTTCGTCTTCAAGAATTAAAAGGATCTAGGTGAAGATCCTTTTTGATAA
TCTCATGACCAAAATCCCTTAACGTGAGTTTTCGTTCCACTGAGCGTCAGACCCCGTAGAAAAGATCAAAGG
ATCTTCTTGAGATCCTTTTTTTCTGCGCGTAATCTGCTGCTTGCAAACAAAAAAACCACCGCTACCAGCGGT
GGTTTGTTTGCCGGATCAAGAGCTACCAACTCTTTTTCCGAAGGTAACTGGCTTCAGCAGAGCGCAGATACC
```

FIG. 8A

```
AAATACTGTCCTTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTGCACACAGCCCAGCTTGGAGCG
AACGACCTACACCGAACTGAGATACCTACAGCGTGAGCATTGAGAAAGCGCCACGCTTCCCGAAGGGAGAAA
GGCGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCTTTGAGTGAGCTGATAC
CGCTCGCCGCAGCCGAACGACCGAGCGCAGCGAGTCAGTGAGCGAGGAAGCGGAAGAGCGCCTGATGCGGTA
TTTTCTCCTTACGCATCTGTGCGGTATTTCACACCGCATATGGTGCACTCTCAGTACAATCTGCTCTGATGC
CGCATAGTTAAGCCAGTATATACACTCCGCTATCGCTACGTGACTGGGTCATGGCTGCGCCCCGACACCCGC
CAACACCCGCTGACGCGCCCTGACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCGAGGCCCAGCTGGCTTATCGAAA
TTAATACGACTCACTATAGGGAGACCGGAATTCGAGCTCGCCCGGGGATCCGTGAGCGGATAACAATTTCAC
ACAGGAAACAGGGGGCAACG
```

*FIG. 8B*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 5062 base pairs
      (B) TYPE: nucleic acid
      (C) STRANDEDNESS: single
      (D) TOPOLOGY: linear (ii) SEQUENCE DESCRIPTION: SEQ ID NO: 1:

```
GTGATTTCTT ATGACAACTA CGTCACCATC CTTGATGAAG AAACACTGAA AGCGTGGATT      60
GCGAAGCTGG AAAAAGCGCC GGTATTTGCA TTTGATACCG AAACCGACAG CCTTGATAAC     120
ATCTCTGCTA ACCTGGTCGG GCTTTCTTTT GCTATCGAGC CAGGCGTAGC GGCATATATT     180
CCGGTTGCTC ATGATTATCT TGATGCGCCC GATCAAATCT CTCGCGAGCG TGCACTCGAG     240
TTGCTAAAAC CGCTGCTGGA AGATGAAAAG GCGCTGAAGG TCGGGCAAAA CCTGAAATAC     300
GATCGCGGTA TTCTGGCGAA CTACGGCATT GAACTGCGTG GGATTGCGTT TGATACCATG     360
CTGGAGTCCT ACATTCTCAA TAGCGTTGCC GGGCGTCACG ATATGGACAG CCTCGCGGAA     420
CGTTGGTTGA AGCACAAAAC CATCACTTTT GAAGAGATTG CTGGTAAAGG CAAAAATCAA     480
CTGACCTTTA ACCAGATTGC CCTCGAAGAA GCCGACGTT ACGCCGCCGA AGATGCAGAT      540
GTCACCTTGC AGTTGCATCT GAAAATGTGG CCGGATCTGC AAAAACACAA AGGGCCGTTG     600
AACGTCTTCG AGAATATCGA AATGCCGCTG GTGCCGGTGC TTTCACGCAT GAACGTAAC      660
GGTGTGAAGA TCGATACAAA AGCAATCGAA GAGTTGTACG TAGAGTTAGC TGCTCGCCGC     720
TCTGAGTTGC TCCGTAAATT GACCGAAACG TTCGGCTCGT GGTATCAGCC TAAAGGTGGC     780
ACTGAGATGT TCTGCCATCC GCGAACAGGT AAGCCACTAC CTAAATACCC TCGCATTAAG     840
ACACCTAAAG TTGGTGGTAT CTTTAAGAAG CCTAAGAACA AGGCACAGCG AGAAGGCCGT     900
GAGCCTTGCG AACTTGATAC CCGCGAGTAC GTTGCTGGTG CTCCTTACAC CCCAGTTGAA     960
CATGTTGTGT TTAACCCTTC GTCTCGTGAC CACATTCAGA AGAAACTCCA AGAGGCTGGG    1020
TGGGTCCCGA CCAAGTACAC CGATAAGGGT GGCGCGCCGT CAACGTCGGA AGAGGTACTG    1080
GAAGAACTGG CGCTGGACTA TCCGTTGCCA AAAGTGATTC TGGAGTATCG TGGTCTGGCG    1140
AAGCTGAAAT CGACCTACAC CGACAAGCTG CCGCTGATGA TCAACCCGAA AACCGGGCGT    1200
GTGCATACCT CTTATCACCA GGCAGTAACT GCAACGGGAC GTTTATCGTC AACCGATCCT    1260
AACCTGCAAA ACATTCCGGT GCGTAACGAA GAAGGTCGTC GTATCCGCCA GGCGTTTATT    1320
GCGCCAGAGG ATTATGTGAT TGTCTCAGCG GACTACTCGC AGATTGAACT GCGCATTATG    1380
GCGCATCTTT CGCGTGACAA AGGCTTGCTG ACCGCATTCG CGGAAGGAAA AGATATCCAC    1440
CGGGCAACGG CGGCAGAAGT GTTTGGTTTG CCACTGGAAA CCGTCACCAG CGAGCAACGC    1500
CGTAGCGCGA AAGCGATCAA CTTTGGTCTG ATTTATGGCA TGAGTGCTTT CGGTCTGGCG    1560
CGGCAATTGA ACATTCCACG TAAAGAAGCG CAGAAGTACA TGGACCTTTA CTTCGAACGC    1620
TACCCTGGCG TGCTGGAGTA TATGGAACGC ACCCGTGCTC AGGCGAAAGA GCAGGGCTAC    1680
GTTGAAACGC TGGACGGACG CCGTCTGTAT CTGCCGGATA TCAAATCCAG CAATGGTGCT    1740
CGTCGTGCAG CGGCTGAACG TGCAGCCATT AACGCGCCAA TGCAGGGAAC CGCCGCCGAC    1800
ATTATCAAAC GGGCGATGAT TGCCGTTGAT GCGTGGTTAC AGGCTGAGCA ACCGCGTGTA    1860
```

-continued

```
CGTATGATCA TGCAGGTACA CGATGAACTG GTATTTGAAG TTCATAAAGA TGATGTTGAT    1920

GCCGTCGCGA AGCAGATTCA TCAACTGATG GAAAACTGTA CCCGTCTGGA TGTGCCGTTG    1980

CTGGTGGAAG TGGGGAGTGG CGAAAACTGG GATCAGGCGC ACTAAGATTC GCCTGAACAT    2040

GCCTTTTTTC GTAAGTAAGC AACATAAGCT GTCACGTTTT GTGATGGCTA TTAGAAATTC    2100

CTATGCAACA ACTGAAAAAA AATTACAAAA AGTGCTTTCT GAACTGAACA AAAAAGAGTA    2160

AAGTTAGTCG CGTAGGGTAC AGAGGTAAGA TGTTCTATCT TTCAGACCTT TTACTTCACG    2220

TAATCGGATT TGGCTGAATA TTTTAGCCGC CCCAGTCAGT AATGACTGGG GCGTTTTTTA    2280

TTGGGCGAAA GAAAAGATCC GTAATGCCTG ATGCGCTATG TTTATCAGGC CAACGGTAGA    2340

ATTGTAATCT ATTGAATTTA CGGGCCGGAT ACGCCACATC CGGCACAAGC ATTAAGGCAA    2400

GAAAATTATT CGCCGTCCTG CGTTTCTTCT ACAGGCTGCA TCTCGCTAAA CCAGGTATCC    2460

AGTTTCTGCC GCAGCTTGTC CACGCCTTGT TTCTTCAACG AAGAAAACGT TTCAACCTGC    2520

ACATCACCGT TAAACGCCAG TACAGCTTCA CGCACCATAT TCAATTGCGC TTTACGTGCG    2580

CCGCTTGCCA GTTTGTCCGC TTTGGTCAGC AGCACCAGAA CGGCGATATT GCTGTCTAGC    2640

TTATCGCGAT GATAAGCTGT CAAACATGAG AATTAAATCA ATCTAAAGTA TATATGAGTA    2700

AACTTGGTCT GACAGTTACC AATGCTTAAT CAGTGAGGCA CCTATCTCAG CGATCTGTCT    2760

ATTTCGTTCA TCCATAGTTG CCTGACTCCC CGTCGTGTAG ATAACTACGA TACGGGAGGG    2820

CTTACCATCT GGCCCCAGTG CTGCAATGAT ACCGCGAGAC CCACGCTCAC CGGCTCCAGA    2880

TTTATCAGCA ATAAACCAGC CAGCCGGAAG GGCCGAGCGC AGAAGTGGTC CTGCAACTTT    2940

ATCCGCCTCC ATCCAGTCTA TTAATTGTTG CCGGGAAGCT AGAGTAAGTA GTTCGCCAGT    3000

TAATAGTTTG CGCAACGTTG TTGCCATTGC TACAGGCATC GTGGTGTCAC GCTCGTCGTT    3060

TGGTATGGCT TCATTCAGCT CCGGTTCCCA ACGATCAAGG CGAGTTACAT GATCCCCCAT    3120

GTTGTGCAAA AAAGCGGTTA GCTCCTTCGG TCCTCCGATC GTTGTCAGAA GTAAGTTGGC    3180

CGCAGTGTTA TCACTCATGG TTATGGCAGC ACTGCATAAT TCTCTTACTG TCATGCCATC    3240

CGTAAGATGC TTTTCTGTGA CTGGTGAGTA CTCAACCAAG TCATTCTGAG AATAGTGTAT    3300

GCGGCGACCG AGTTGCTCTT GCCCGGCGTC AACACGGGAT AATACCGCGC CACATAGCAG    3360

AACTTTAAAA GTGCTCATCA TTGGAAAACG TTCTTCGGGG CGAAAACTCT CAAGGATCTT    3420

ACCGCTGTTG AGATCCAGTT CGATGTAACC CACTCGTGCA CCCAACTGAT CTTCAGCATC    3480

TTTTACTTTC ACCAGCGTTT CTGGGTGAGC AAAAACAGGA AGGCAAAATG CCGCAAAAAA    3540

GGGAATAAGG GCGACACGGA AATGTTGAAT ACTCATACTC TTCCTTTTTC AATATTATTG    3600

AAGCATTTAT CAGGGTTATT GTCTCATGAG CGGATACATA TTTGAATGTA TTTAGAAAAA    3660

TAAACAAATA GGGGTTCCGC GCACATTTCC CCGAAAAGTG CCACCTGACG TCTAAGAAAC    3720

CATTATTATC ATGACATTAA CCTATAAAAA TAGGCGTATC ACGAGGCCCT TTCGTCTTCA    3780

AGAATTAAAA GGATCTAGGT GAAGATCCTT TTTGATAATC TCATGACCAA AATCCCTTAA    3840

CGTGAGTTTT CGTTCCACTG AGCGTCAGAC CCCGTAGAAA AGATCAAAGG ATCTTCTTGA    3900

GATCCTTTTT TTCTGCGCGT AATCTGCTGC TTGCAAACAA AAAAACCACC GCTACCAGCG    3960

GTGGTTTGTT TGCCGGATCA AGAGCTACCA ACTCTTTTTC CGAAGGTAAC TGGCTTCAGC    4020

AGAGCGCAGA TACCAAATAC TGTCCTTCTA GTGTAGCCGT AGTTAGGCCA CCACTTCAAG    4080

AACTCTGTAG CACCGCCTAC ATACCTCGCT CTGCTAATCC TGTTACCAGT GGCTGCTGCC    4140

AGTGGCGATA AGTCGTGTCT TACCGGGTTG GACTCAAGAC GATAGTTACC GGATAAGGCG    4200

CAGCGGTCGG GCTGAACGGG GGGTTCGTGC ACACAGCCCA GCTTGGAGCG AACGACCTAC    4260
```

-continued

```
ACCGAACTGA GATACCTACA GCGTGAGCAT TGAGAAAGCG CCACGCTTCC CGAAGGGAGA      4320

AAGGCGGACA GGTATCCGGT AAGCGGCAGG GTCGGAACAG GAGAGCGCAC GAGGGAGCTT      4380

CCAGGGGGAA ACGCCTGGTA TCTTTATAGT CCTGTCGGGT TTCGCCACCT CTGACTTGAG      4440

CGTCGATTTT TGTGATGCTC GTCAGGGGGG CGGAGCCTAT GGAAAAACGC CAGCAACGCG      4500

GCCTTTTTAC GGTTCCTGGC CTTTTGCTGG CCTTTTGCTC ACATGTTCTT TCCTGCGTTA      4560

TCCCCTGATT CTGTGGATAA CCGTATTACC GCCTTTGAGT GAGCTGATAC CGCTCGCCGC      4620

AGCCGAACGA CCGAGCGCAG CGAGTCAGTG AGCGAGGAAG CGGAAGAGCG CCTGATGCGG      4680

TATTTTCTCC TTACGCATCT GTGCGGTATT TCACACCGCA TATGGTGCAC TCTCAGTACA      4740

ATCTGCTCTG ATGCCGCATA GTTAAGCCAG TATATACACT CCGCTATCGC TACGTGACTG      4800

GGTCATGGCT GCGCCCCGAC ACCCGCCAAC ACCCGCTGAC GCGCCCTGAC GGGCTTGTCT      4860

GCTCCCGGCA TCCGCTTACA GACAAGCTGT GACCGTCTCC GGGAGCTGCA TGTGTCAGAG      4920

GTTTTCACCG TCATCACCGA AACGCGCGAG GCCCAGCTGG CTTATCGAAA TTAATACGAC      4980

TCACTATAGG GAGACCGGAA TTCGAGCTCG CCCGGGATC CGTGAGCGGA TAACAATTTC       5040

ACACAGGAAA CAGGGGGCAA CG                                              5062
```

(2) INFORMATION FOR SEQ ID NO: 2:

(i) SEQUENCE CHARACTERISTICS:
        (A) LENGTH:        5060 base pairs
        (B) TYPE:          nucleic acid
        (C) STRANDEDNESS:  single
        (D) TOPOLOGY:     linear (xi) SEQUENCE DESCRIPTION: SEQ ID NO: 2:

```
GTGATTTCTT ATGACAACTA CGTCACCATC CTTGATGAAG AAACACTGAA AGCGTGGATT        60

GCGAAGCTGG AAAAAGCGCC GGTATTTGCA TTTGATACCG AAACCGACAG CCTTGATAAC       120

ATCTCTGCTA ACCTGGTCGG GCTTTCTTTT GCTATCGAGC CAGGCGTAGC GGCATATATT       180

CCGGTTGCTC ATGATTATCT TGATGCGCCC GATCAAATCT CTCGCGAGCC TGCACTCGAG       240

TTGCTAAAAC CGCTGCTGGA AGATGAAAAG GCGCTGAAGG TCGGGCAAAA CCTGAAATAC       300

GATCGCGGTA TTCTGGCGAA CTACGGCATT GAACTGCGTG GGATTGCGTT TGATACCATG       360

CTGGAGTCCT ACATTCTCAA TAGCGTTGCC GGGCGTCACG ATATGGACAG CCTCGCGGAA       420

CGTTGGTTGA AGCACAAAAC CATCACTTTT GAAGAGATTG CTGGTAAAGG CAAAAATCAA       480

CTGACCTTTA ACCAGATTGC CCTCGAAGAA GCCGGACGTT ACGCCGCCGA AGATGCAGAT       540

GTCACCTTGC AGTTGCATCT GAAAATGTGG CCGGATCTGC AAAAACACAA AGGGCCGTTG       600

AACGTCTTCG AGAATATCGA AATGCCGCTG GTGCCGGTGC TTTCACGCAT TGAACGTAAC       660

GGTGTGAAGA TCGATCCGAA AGTGCTGCAC AATCATTCTG AAGAGCTCAC CCTTCGTCTG       720

GCTGAGCTGG AAAAGAAAGC GACCGAAACG TTCGGCTCGT GGTATCAGCC TAAAGGTGGC       780

ACTGAGATGT TCTGCCATCC GCGAACAGGT AAGCCACTAC CTAAATACCC TCGCATTAAG       840

ACACCTAAAG TTGGTGGTAT CTTTAAGAAG CCTAAGAACA AGGCACAGCG AGAAGGCCGT       900

GAGCCTTGCG AACTTGATAC CCGCGAGTAC GTTGCTGGTG CTCCTTACAC CCCAGTTGAA       960

CATGTTGTGT TTAACCTTTC TTCCACCAAG CAGTTACAAA CCATTCTCTT TGAAAAACAG      1020

GGCATTAAAC CGCTGAAGAA AACGCCGGGT GGCGCGCCGT CAACGTCGGA AGAGGTACTG      1080

GAAGAACTGG CGCTGGACTA TCCGTTGCCA AAAGTGATTC TGGAGTATCG TGGTCTGGCG      1140

AAGCTGAAAT CGACCTACAC CGACAAGCTG CCGCTGATGA TCAACCCGAA AACCGGGCGT      1200

GTGCATACCT CTTATCACCA GGCAGTAACT GCAACGGGAC GTTTATCGTC AACCGATCCT      1260
```

```
AACCTGCAAA ACATTCCGGT GCGTAACGAA GAAGGTCGTC GTATCCGCCA GGCGTTTATT    1320

GCGCCAGAGG ATTATGTGAT TGTCTCAGCG GACTACTCGC AGATTGAACT GCGCATTATG    1380

GCGCATCTTT CGCGTGACAA AGGCTTGCTG ACCGCATTCG CGGAAGGAAA AGATATCCAC    1440

CGGGCAACGG CGGCAGAAGT GTTTGGTTTG CCACTGGAAA CCGTCACCAG CGAGCAACGC    1500

CGTAGCGCGA AAGCGATCAA CTTTGGTCTG ATTTATGGCA TGAGTGCTTT CGGTCTGGCG    1560

CGGCAATTGA ACATTCCACG TAAAGAAGCG CAGAAGTACA TGGACCTTTA CTTCGAACGC    1620

TACCCTGGCG TGCTGGAGTA TATGGAACGC ACCCGTGCTC AGGCGAAAGA GCAGGGCTAC    1680

GTTGAAACGC TGGACGGACG CCGTCTGTAT CTGCCGGATA TCAAATCCAG CAATGGTGCT    1740

CGTCGTGCAG CGGCTGAACG TGCAGCCATT AACGCGCCAA TGCAGGGAAC CGCCGCCGAC    1800

ATTATCAAAC GGGCGATGAT TGCCGTTGAT GCGTGGTTAC AGGCTGAGCA ACCGCGTGTA    1860

CGTATGATCA TGCAGGTACA CGATGAACTG GTATTTGAAG TTCATAAAGA TGATGTTGAT    1920

GCCGTCGCGA AGCAGATTCA TCAACTGATG GAAAACTGTA CCCGTCTGGA TGTGCCGTTG    1980

CTGGTGGAAG TGGGGAGTGG CGAAAACTGG GATCAGGCGC ACTAAGATTC GCCTGAACAT    2040

GCCTTTTTTC GTAAGTAAGC AACATAAGCT GTCACGTTTT GTGATGGCTA TTAGAAATTC    2100

CTATGCAACA ACTGAAAAAA AATTACAAAA AGTGCTTTCT GAACTGAACA AAAAGAGTA    2160

AAGTTAGTCG CGTAGGGTAC AGAGGTAAGA TGTTCTATCT TTCAGACCTT TTACTTCACG    2220

TAATCGGATT TGGCTGAATA TTTTAGCCGC CCCAGTCAGT AATGACTGGG GCGTTTTTA    2280

TTGGGCGAAA GAAAAGATCC GTAATGCCTG ATGCGCTATG TTTATCAGGC CAACGGTAGA    2340

ATTGTAATCT ATTGAATTTA CGGGCCGGAT ACGCCACATC CGGCACAAGC ATTAAGGCAA    2400

GAAAATTATT CGCCGTCCTG CGTTTCTTCT ACAGGCTGCA TCTCGCTAAA CCAGGTATCC    2460

AGTTTCTGCC GCAGCTTGTC CACGCCTTGT TTCTTCAACG AAGAAAACGT TTCAACCTGC    2520

ACATCACCGT TAAACGCCAG TACAGCTTCA CGCACCATAT TCAATTGCGC TTTACGTGCG    2580

CCGCTTGCCA GTTTGTCCGC TTTGGTCAGC AGCACCAGAA CGGCGATATT GCTGTCTAGC    2640

TTATCGATGA TAAGCTGTCA AACATGAGAA TTAAATCAAT CTAAAGTATA TATGAGTAAA    2700

CTTGGTCTGA CAGTTACCAA TGCTTAATCA GTGAGGCACC TATCTCAGCG ATCTGTCTAT    2760

TTCGTTCATC CATAGTTGCC TGACTCCCCG TCGTGTAGAT AACTACGATA CGGGAGGGCT    2820

TACCATCTGG CCCCAGTGCT GCAATGATAC CGCGAGACCC ACGCTCACCG GCTCCAGATT    2880

TATCAGCAAT AAACCAGCCA GCCGGAAGGG CCGAGCGCAG AAGTGGTCCT GCAACTTTAT    2940

CCGCCTCCAT CCAGTCTATT AATTGTTGCC GGGAAGCTAG AGTAAGTAGT TCGCCAGTTA    3000

ATAGTTTGCG CAACGTTGTT GCCATTGCTA CAGGCATCGT GGTGTCACGC TCGTCGTTTG    3060

GTATGGCTTC ATTCAGCTCC GGTTCCCAAC GATCAAGGCG AGTTACATGA TCCCCCATGT    3120

TGTGCAAAAA AGCGGTTAGC TCCTTCGGTC CTCCGATCGT TGTCAGAAGT AAGTTGGCCG    3180

CAGTGTTATC ACTCATGGTT ATGGCAGCAC TGCATAATTC TCTTACTGTC ATGCCATCCG    3240

TAAGATGCTT TTCTGTGACT GGTGAGTACT CAACCAAGTC ATTCTGAGAA TAGTGTATGC    3300

GGCGACCGAG TTGCTCTTGC CCGGCGTCAA CACGGGATAA TACCGCGCCA CATAGCAGAA    3360

CTTTAAAAGT GCTCATCATT GGAAAACGTT CTTCGGGGCG AAAACTCTCA AGGATCTTAC    3420

CGCTGTTGAG ATCCAGTTCG ATGTAACCCA CTCGTGCACC CAACTGATCT TCAGCATCTT    3480

TTACTTTCAC CAGCGTTTCT GGGTGAGCAA AAACAGGAAG GCAAAATGCC GCAAAAAAGG    3540

GAATAAGGGC GACACGGAAA TGTTGAATAC TCATACTCTT CCTTTTTCAA TATTATTGAA    3600

GCATTTATCA GGGTTATTGT CTCATGAGCG GATACATATT TGAATGTATT TAGAAAAATA    3660
```

-continued

```
AACAAATAGG GGTTCCGCGC ACATTTCCCC GAAAAGTGCC ACCTGACGTC TAAGAAACCA  3720

TTATTATCAT GACATTAACC TATAAAAATA GGCGTATCAC GAGGCCCTTT CGTCTTCAAG  3780

AATTAAAAGG ATCTAGGTGA AGATCCTTTT TGATAATCTC ATGACCAAAA TCCCTTAACG  3840

TGAGTTTTCG TTCCACTGAG CGTCAGACCC CGTAGAAAAG ATCAAAGGAT CTTCTTGAGA  3900

TCCTTTTTTT CTGCGCGTAA TCTGCTGCTT GCAAACAAAA AAACCACCGC TACCAGCGGT  3960

GGTTTGTTTG CCGGATCAAG AGCTACCAAC TCTTTTTCCG AAGGTAACTG GCTTCAGCAG  4020

AGCGCAGATA CCAAATACTG TCCTTCTAGT GTAGCCGTAG TTAGGCCACC ACTTCAAGAA  4080

CTCTGTAGCA CCGCCTACAT ACCTCGCTCT GCTAATCCTG TTACCAGTGG CTGCTGCCAG  4140

TGGCGATAAG TCGTGTCTTA CCGGGTTGGA CTCAAGACGA TAGTTACCGG ATAAGGCGCA  4200

GCGGTCGGGC TGAACGGGGG GTTCGTGCAC ACAGCCCAGC TTGGAGCGAA CGACCTACAC  4260

CGAACTGAGA TACCTACAGC GTGAGCATTG AGAAAGCGCC ACGCTTCCCG AAGGGAGAAA  4320

GGCGGACAGG TATCCGGTAA GCGGCAGGGT CGGAACAGGA GAGCGCACGA GGGAGCTTCC  4380

AGGGGGAAAC GCCTGGTATC TTTATAGTCC TGTCGGGTTT CGCCACCTCT GACTTGAGCG  4440

TCGATTTTTG TGATGCTCGT CAGGGGGGCG GAGCCTATGG AAAAACGCCA GCAACGCGGC  4500

CTTTTTACGG TTCCTGGCCT TTTGCTGGCC TTTTGCTCAC ATGTTCTTTC CTGCGTTATC  4560

CCCTGATTCT GTGGATAACC GTATTACCGC CTTTGAGTGA GCTGATACCG CTCGCCGCAG  4620

CCGAACGACC GAGCGCAGCG AGTCAGTGAG CGAGGAAGCG GAAGAGCGCC TGATGCGGTA  4680

TTTTCTCCTT ACGCATCTGT GCGGTATTTC ACACCGCATA TGGTGCACTC TCAGTACAAT  4740

CTGCTCTGAT GCCGCATAGT TAAGCCAGTA TATACACTCC GCTATCGCTA CGTGACTGGG  4800

TCATGGCTGC GCCCCGACAC CCGCCAACAC CCGCTGACGC GCCCTGACGG GCTTGTCTGC  4860

TCCCGGCATC CGCTTACAGA CAAGCTGTGA CCGTCTCCGG GAGCTGCATG TGTCAGAGGT  4920

TTTCACCGTC ATCACCGAAA CGCGCGAGGC CCAGCTGGCT TATCGAAATT AATACGACTC  4980

ACTATAGGGA GACCGGAATT CGAGCTCGCC CGGGGATCCG TGAGCGGATA ACAATTTCAC  5040

ACAGGAAACA GGGGGCAACG                                              5060
```

DNA POLYMERASE WITH MODIFIED PROCESSIVITY

This application is a continuation-in-part of U.S. Ser. No. 08/599,224, filed Feb. 9, 1996, entitled "DNA Polymerase with Modified Processivity", now abandoned.

This invention is supported by DOE Contract No. DE-GF02-88ER-60688 and the government has certain rights to the invention.

BACKGROUND OF THE INVENTION

This invention relates to DNA polymerases, and in particular those having a processivity greater than that of DNA polymerase I of *Escherichia coli*.

Processivity is a measurement of the ability of a DNA polymerase to incorporate one or more deoxynucleotides into a primer template molecule without the DNA polymerase dissociating from that molecule. DNA polymerases having low processivity, such as the Klenow fragment of DNA polymerase I of *E. coli*, will dissociate after about 5–40 nucleotides are incorporated on average. Other polymerases, such as T7 DNA polymerase in the presence of thioredoxin, are able to incorporate many thousands of nucleotides prior to dissociating. In the absence of thioredoxin such a T7 DNA polymerase has a much lower processivity. Such processivity can be measured much as described by Tabor et al., JBC 262, 16212 (1987) and is thought to be advantageous in certain biochemical reactions such as DNA sequencing (see, Tabor U.S. Pat. No. 4,795,699).

As stated above, the T7 DNA polymerase (T7 gene 5 protein) by itself has low processivity. T7 gene 5 protein, however, binds tightly to a processivity factor, the host-encoded thioredoxin, in a one-to-one ratio. Thioredoxin stabilizes the binding of T7 DNA polymerase specifically to a primer-template, and the complex of the two proteins is highly processive, and is capable of extending a primer many hundreds of nucleotides without dissociating (Tabor et al, supra; Huber et al., JBC 262, 16224 (1987)).

SUMMARY OF THE INVENTION

This invention relates to novel chimeric proteins which are particularly well adapted for use in amplification reactions (such as the polymerase chain reaction) and related reactions, as well as in DNA sequencing. Applicant has determined that the processivity of a DNA polymerase can be significantly increased (or if desired, decreased) by modifying an existing DNA polymerase to have a non-naturally associated processivity factor binding site. Such processivity factor binding sites bind factors which will enhance processivity of the DNA polymerase, e.g., thioredoxin. Below are provided examples of DNA polymerases which in their natural state are not affected by the presence of a processivity factor, but when modified to form a chimeric protein have their processivity increased many fold in the presence of such a processivity factor.

Those in the art will recognize that many equivalent chimeric molecules can now be readily created using the teachings in this application. Thus, for example, thermostable DNA polymerases can now be created having increased processivity. The examples provided below are of a polI-type DNA polymerase into which is inserted a polI-type processivity factor binding domain. Thus, it will now be readily apparent how other polI-type polymerases (such as that present in *Thermus aquaticus*) can be modified to include such polI-type processivity factor binding domains.

In this way, a thermostable processive DNA polymerase can be created. As noted above, such a polymerase will have advantages over existing polymerases in DNA sequencing and amplification reactions. While the specific activity of the DNA polymerase in the chimeric protein may be less than that of the unmodified protein, the increased processivity of such a polymerase outweighs such loss in activity.

Thus, in a first aspect, the invention features a chimeric DNA polymerase having a DNA polymerase domain and a processivity factor binding domain not naturally associated with the DNA polymerase domain.

By "chimeric" is meant that the DNA polymerase includes one or several amino acids (not present in a corresponding wild-type polymerase) which either modify an existing processivity factor binding domain or introduce a new processivity factor binding domain into the DNA polymerase. While it may be useful to remove amino acids from the wild-type DNA polymerase and replace them with a processivity factor binding domain, this is not essential in practice of the invention. Generally, such a chimeric DNA polymerase will have inserted therein at least 20 or more amino acids, preferably at least 50 or even 100 amino acids in a corresponding naturally occurring DNA polymerase.

By "not naturally-associated" is meant that the processivity factor binding domain cannot be found in nature associated with the DNA polymerase domain. Thus, such a chimeric DNA polymerase is a man-made object and is not found in nature as a wild-type polymerase. The region to be inserted as described herein is usually not naturally-occurring in the enzyme in which it is inserted but is taken from an enzyme in which it naturally occurs.

By "processivity factor" is meant a protein or polypeptide which is able to increase the processivity of a DNA polymerase by at least two and preferably 20, 50 or more fold. Such a processivity factor generally binds to the DNA polymerase and thereby increases the processivity of that polymerase. A "binding domain" refers to that portion of a DNA polymerase which is involved in binding of a processivity factor, as can be measured by standard procedures, examples of which are provided below. While examples of specific domains are provided below, those in the art can use standard procedures to determine other such domains, or use a larger or smaller portions of the domains exemplified.

In preferred embodiments, the chimeric DNA polymerase has a DNA polymerase domain which is thermophilic, e.g., is the DNA polymerase domain present in a thermophilic DNA polymerase, such as one from the DNA polymerase in *Thermus aquaticus*, *Thermus thermophilus*, Vent DNA polymerase, or *Bacillus sterothermophilus* DNA polymerase; the processivity factor when bound to the DNA polymerase causes an increase in the processivity of the chimeric DNA polymerase, e.g., the processivity factor is thioredoxin; and the chimeric DNA polymerase consists essentially of the amino acid sequence of a wild-type DNA polymerase having inserted therein a processivity factor binding domain of a different DNA polymerase, e.g., the processivity factor binding domain is that present in a T7-type DNA polymerase, (see Tabor, U.S. Patent, supra, hereby incorporated by reference herein). As will be recognized, the processivity factor binding domain may also be placed into non-thermophilic polymerases, such as Klenow fragment of *E. coli* DNA polymerase I as shown below.

In other preferred embodiments, the processivity factor binding domain consists essentially of amino acids 236 to 363 from T7 gene 5 protein; the polymerase consists essentially of a wild-type DNA polymerase having substituted therein for a portion of the wild-type DNA polymerase, a processivity factor binding domain; the processivity factor binding domain corresponds essentially to amino acids 236 to 363 of T7 gene 5 protein substituted in a region of the wild-type DNA polymerase corresponding to about amino acids 549 to 609 of Klenow fragment of DNA polymerase I; and the processivity factor binding domain binds a processivity factor and thereby increases the processivity of the chimeric DNA polymerase by at least 10-fold compared to in the absence of the processivity factor.

In further preferred embodiments, the processivity factor binding domain consists essentially of amino acid residues 258 to 333 of T7 DNA polymerase; the processivity factor binding domain corresponds essentially to amino acid residues 258 to 333 of T7 gene 5 protein substituted in a region of the wild-type DNA polymerase corresponding to about amino acid residues 571 to 577 of E. coli DNA polymerase I or amino acid residues 475 to 481 of Taq DNA polymerase, and the processivity factor binding domain binds a processivity factor and thereby increases the processivity of the chimeric DNA polymerase by at least four-fold compared to the wild-type DNA polymerase in the absence of the thioredoxin binding domain.

In a related aspect, the processivity factor consists of a protein modified to increase its heat stability. In preferred embodiments, the processivity factor is thioredoxin and the mutation is a change of aspartic acid 26 to alanine.

In another related aspect, a processivity factor binding domain is inserted into Tth DNA polymerase in order to increase its processivity as a reverse transcriptase. Such a polymerase is useful in an improved method for reverse transcription. In preferred embodiments, the processivity factor binding domain consists of essentially amino acid residues 258 to 333 of T7 gene 5 protein that are substituted in place of essentially amino acid residues 477 to 483 of Tth DNA polymerase.

In a further related aspect, the invention features a method for constructing a chimeric DNA polymerase having a non-naturally associated processivity factor binding domain. The method involves creating a recombinant nucleic acid encoding a DNA polymerase having inserted therein a processivity factor binding domain-encoding region not naturally associated with the DNA polymerase encoding domain. In preferred embodiments the presence of the processivity factor results in an increase in the processivity of the chimeric DNA polymerase to which it binds, the processivity factor is thioredoxin, the processivity binding domain is derived from T7 DNA polymerase, the processivity factor binding domain is obtained from a DNA polymerase that is a member of the Pol I family, the processivity factor binding domain is obtained from the DNA polymerase of phage SP01, the processivity factor binding domain is obtained from a DNA polymerase of the pol alpha family, and the DNA polymerase is thermophilic.

In another related aspect, the invention features a method for increasing the processivity of a DNA polymerase by modifying that DNA polymerase to have inserted therein a non-naturally associated processivity factor binding domain.

In a further aspect, the invention features recombinant DNA encoding a chimeric DNA polymerase as described above.

In even further related aspects, the invention features improved methods for amplification or DNA sequencing of nucleic acid, the improvement being the use of a chimeric DNA polymerase having a DNA polymerase domain and a processivity factor binding domain not naturally associated with that DNA polymerase domain. In further improved methods for amplification or DNA sequencing a chimeric thermophilic DNA polymerase having a DNA polymerase domain and a processivity factor binding domain not naturally associated with that DNA polymerase domain is provided with a thermophilic processivity factor for binding to the processivity factor binding domain. In a preferred embodiment the processivity factor binding domain is for thioredoxin and the thermophilic processivity factor is thermophilic thioredoxin.

Other features and advantages of the invention will be apparent from the following description of the preferred embodiments, and from the claims.

DESCRIPTION OF THE PREFERRED EMBODIMENTS

The drawings will first briefly be described.

Drawings

FIG. 1 is a diagrammatic representation of a chimeric polymerase.

FIG. 2A shows surface plasmon resonance analysis of thioredoxin binding to the chip containing anti-thioredoxin antibodies immobilized on the chip. FIG. 2B shows surface plasmon resonance analysis of Klenow fragment binding to the chip containing bound thioredoxin. FIG. 2C shows surface plasmon resonance of the hybrid DNA polymerase binding to the chip containing bound thioredoxin.

Figure 6A:
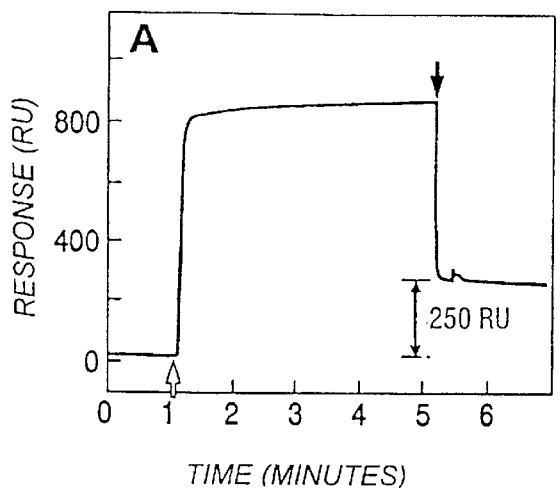
Figure 6B:
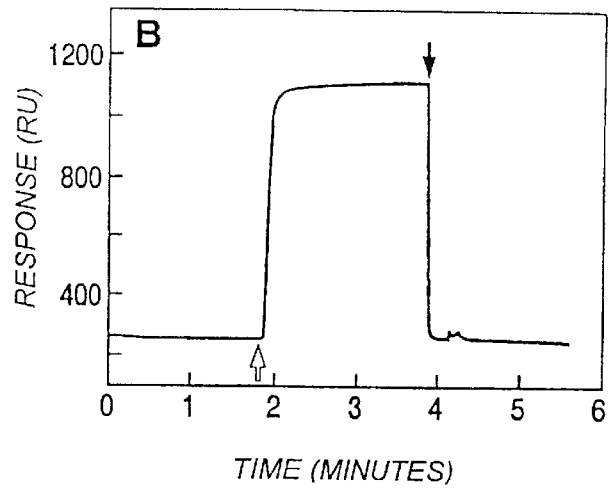
Figure 6C:
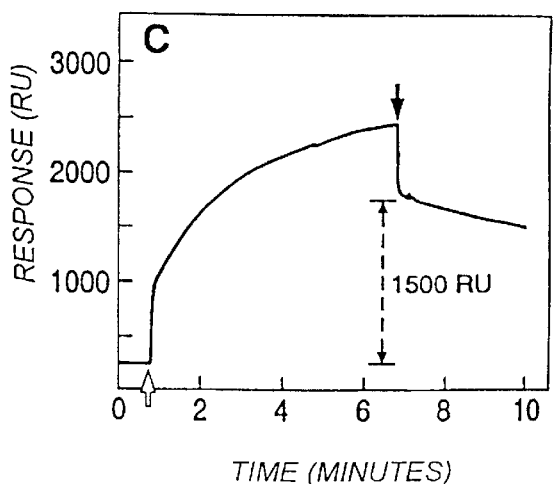

FIG. 6A shows the binding of thioredoxin to the chip containing bound anti-thioredoxin antibody using surface plasmon resonance analysis. FIG. 6B shows the binding of Klenow fragment to the chip containing bound thioredoxin using surface plasmon resonance analysis. FIG. 6C shows the binding of Klenow-TBD1 DNA polymerase to the chip containing bound thioredoxin using surface plasmon resonance analysis.

Figure 7:
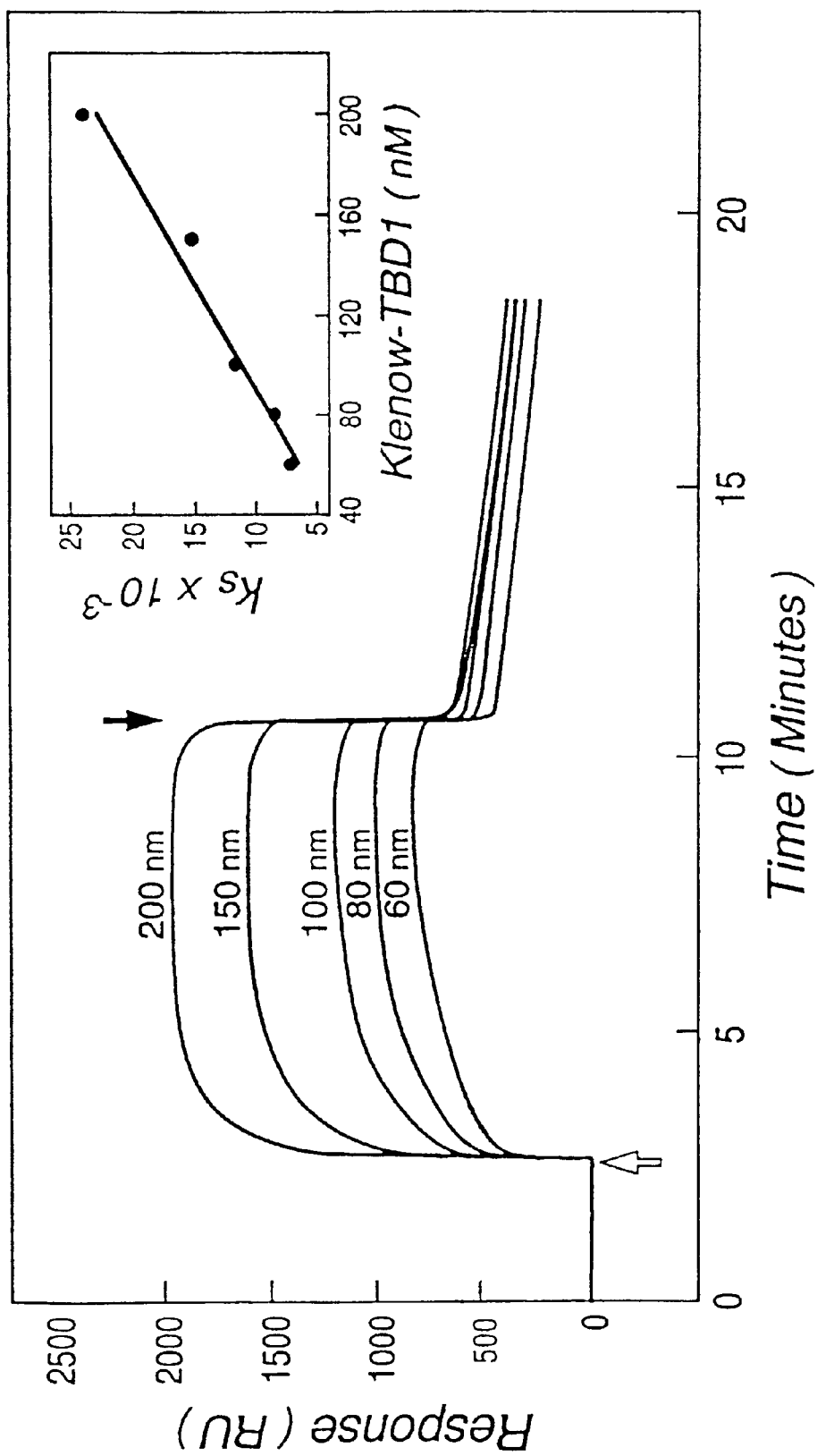

FIG. 7 shows the determination of the binding constant of thioredoxin for Klenow-TBD1 DNA polymerase by surface plasmon resonance analysis.

FIG. 8 shows the sequence of plasmid pKlen-TBD1 which produces the protein Klenow-TBD1.

POLYMERASE DOMAIN which BINDS PROCESSIVITY FACTOR

DNA polymerases may be classified into four families according to their amino acid sequence similarities (Delarue et al, Protein Engineering. 3,461 (1990); Blanco et al. Gene 100, 27 (1991); Braithwaite and Ito, Nucleic Acids Res. 21, 787 (1993)). One family is referred to as the "Pol I-type" DNA polymerases; they include E. coli DNA polymerase I, T7 DNA polymerase, Taq DNA polymerase, mitochondrial DNA polymerases, and the DNA polymerases from phage T5, SP01 and SP02.

The carboxy terminal half of T7 DNA polymerase contains the polymerase active site and the DNA binding domain, while the amino terminal half of T7 DNA polymerase contains the 3' to 5' exonuclease active site. The carboxy terminal half of T7 DNA polymerase shares extensive homology with pol I-type DNA polymerases (Ollis et al, Nature 313, 818 (1985), Lopez et al., JBC. 264,4255 (1989), Braithwaite and Ito, Nucleic Acids Res. 21, 787 (1993)). Alignment of the polymerase domains of pol I-type DNA polymerases reveals that in T7 DNA polymerase there is a region of 75 amino acid residues (residues 258 to 333) that is not present in other pol I-type DNA polymerases, and thus forms an insert between the adjacent, aligned sequences. This unique region in T7 DNA polymerase corresponds to the interhelix-region between helices H and H1 in the three dimensional crystal structure of *E. coli* DNA polymerase I (Beese et al, Science 260, 352 (1993)).

The only other known pol I-type DNA polymerase that has a large insert of amino acid residues at this position is that of phage SP01 (Braithwaite and Ito, Nucleic Acids Res. 21, 787 (1993)); there is minimal homology between the amino acid sequence of the inserts from T7 DNA polymerase and that of SP01 DNA polymerase.

The other known pol I-type DNA polymerases without an insert between the H and H1 helices do not bind thioredoxin, and thioredoxin has no effect on their processivity. Based on these observations, it seemed possible that this region unique to T7 DNA polymerase is responsible for the binding of thioredoxin.

Figure 1:
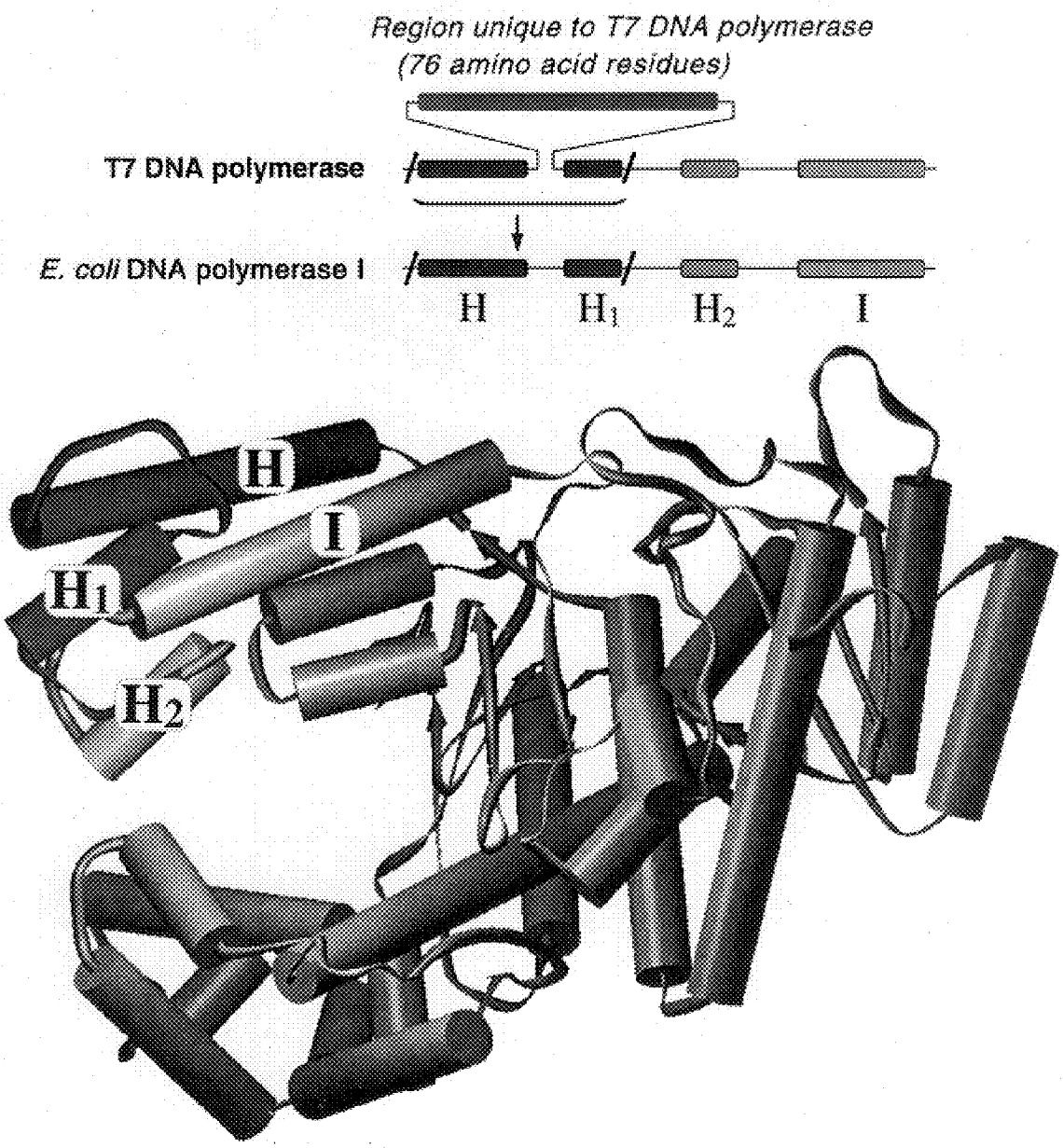

In order to test this hypothesis, we inserted the above-noted region of T7 DNA polymerase into the Klenow fragment, and purified the hybrid DNA polymerase (referred to here as the "hybrid or chimeric DNA polymerase"). The structure of the hybrid DNA polymerase is shown in FIG. 1. The purified hybrid DNA polymerase has low activity and low processivity in the absence of thioredoxin. We demonstrate that thioredoxin binds specifically to the hybrid DNA polymerase, and the binding of thioredoxin to the hybrid DNA polymerase restores the DNA polymerase activity to a nearly normal level, and increases the processivity of the hybrid DNA polymerase by approximately 30-fold.

Equivalent experiments can be performed to determine other such binding domains.

EXAMPLE 1
Forming a Chimeric Polymerase

Referring to FIG. 1, the gene for a chimeric protein in which amino acids 236 to 363 from T7 gene 5 protein were substituted for amino acids 549 to 609 of Klenow fragment was constructed using standard PCR mutagenesis techniques. The sequence of the resulting plasmid (pSE-2) used to overproduce the hybrid DNA polymerase is given as SEQ. ID. NO.: 1.

pSE-2 was transformed into BL21/DE3 cells (Novagen). The cells were grown in the presence of ampicillin and chloramphenicol, and were induced by the addition of IPTG. Most of the overproduced hybrid DNA polymerase was insoluble. The protein was purified by lysing the cells with lysozyme, centrifuging the extract and removing the supernatant, washing the pellet with buffer, and then dissolving the pellet in 6 M urea. The dissolved protein was then dialysed overnight against 1 M NaCl, 30 mM Tris—HCl, pH 7.5, 1 mM DTT and 2 mM EDTA. After dialysis overnight, the NaCl concentration was gradually reduced to 20 mM in three dialysis steps of about four hours each. The protein was then further purified by ion exchange chromatography using an FPLC mono Q column (Pharmacia). The purified hybrid DNA polymerase was dialyzed against 20 mM $KPO_4$, pH 7.5, 0.1 mM EDTA, and 0.1 mM DTT and 50% glycerol and stored at $-20°$ C.

EXAMPLE 2
Relative Specific Activities of the Purified Hybrid DNA Polymerase In the absence of thioredoxin, the hybrid DNA polymerase has low DNA polymerase activity. This activity is stimulated approximately 50-fold by the presence of thioredoxin. T7 DNA polymerase (gene 5 protein), like the hybrid DNA polymerase, has low activity in the absence of thioredoxin and this activity is stimulated approximately 60-fold by the presence of thioredoxin. On the other hand, the DNA polymerase activity of Klenow fragment (without the T7 insert) is the same in the presence and absence of thioredoxin.

Specific polymerase activities were measured as the amount [$^3$H]dTMP incorporated as a function of the amount of enzyme. The reaction mixture (50 µl) contained 40 mM Tris-HCl pH 7.5, 50 mM NaCl, 5 mM DTT, 10 mM $MgCl_2$, 0.3 mM dNTPs (3 cpm/pmole [$^3$H]dTTP) and 0.1 mg/ml heat denatured calf thymus DNA. Where present, thioredoxin was added at a concentration of 10 µM. After an incubation of 10 minutes at 37° C., the reaction mixture was spotted on DE81 filter paper (Whatman), washed, dried and counted in a scintillation counter as described (Bryant et al, Biochemistry 22, 3537 (1983)). The specific activity of the T7 DNA polymerase/thioredoxin complex is arbitrarily defined as 100 units/mg below, and the specific activities of the DNA polymerases determined under identical assay conditions are given relative to this value:

| Enzyme | Specific activity (arbitrary units) /mg |
|---|---|
| T7 DNA polymerase + thioredoxin | [100] |
| T7 DNA polymerase − thioredoxin | 1.7 |
| Klenow fragment + thioredoxin | 73 |
| Klenow fragment − thioredoxin | 73 |
| Hybrid DNA polymerase + thioredoxin | 17 |
| Hybrid DNA polymerase − thioredoxin | 0.3 |

Figure 3:
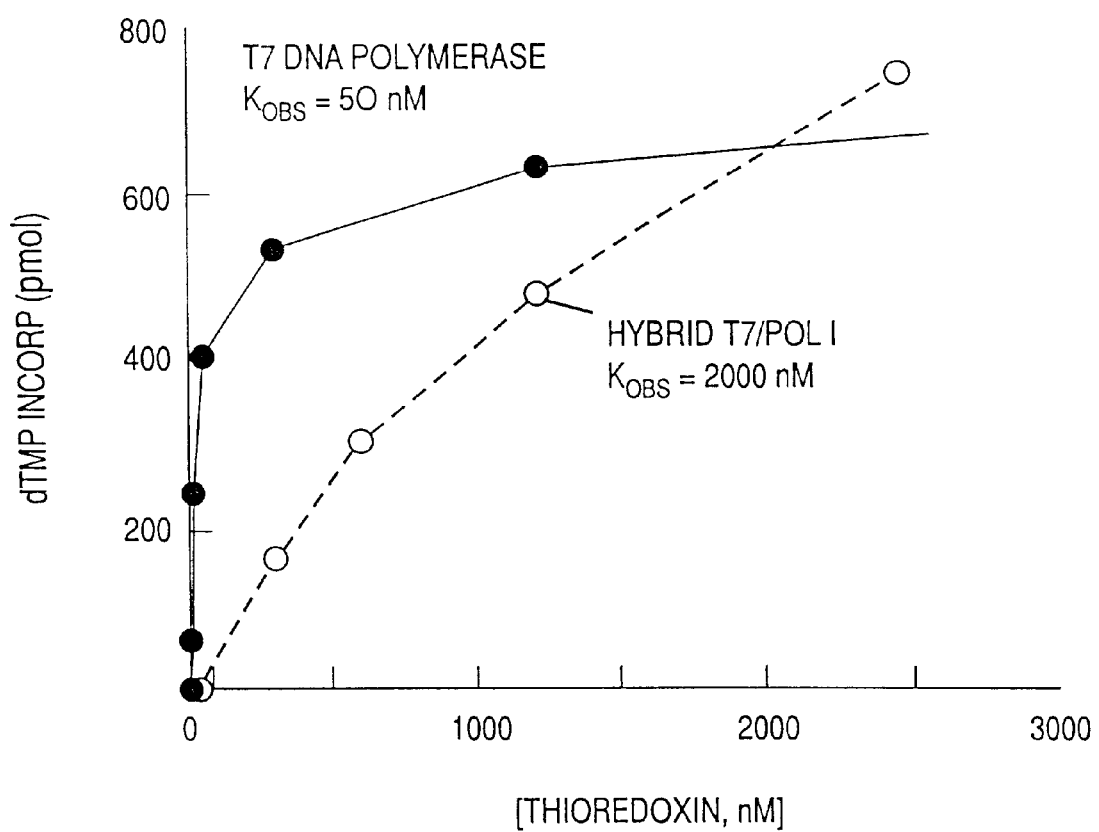
FIG. 3 shows stimulation of DNA synthesis by thioredoxin.

We have measured DNA polymerase as a function of increasing thioredoxin concentration (FIG. 3). Both the T7 DNA polymerase (gene 5 protein) and the hybrid DNA polymerase are stimulated by increasing amounts of thioredoxin.

From these data, Scatchard plots were used to determine the observed equilibrium dissociation constants of T7 DNA polymerase and the hybrid DNA polymerase for thioredoxin, as described by Huber et al. (JBC 261, 15006 (1986)).

For these experiments, the reaction mixtures (50 µl) contained 40 mM Tris-HCl, pH 7.5, 50 mM NaCl, 10 mM $MgCl_2$, 5 mM DTT, 0.3 mM dNTPs (3 cpm/pmole [$^3$H] dTTP) and 0.2 mg/ml alkali denatured salmon sperm DNA. The concentration of the hybrid DNA polymerase used was 30 nM, and the T7 DNA polymerase was 3 nM. Reactions were carried out at 37° C. for either five minutes (T7 DNA polymerase) or 20 minutes (hybrid DNA polymerase).

After completion of the reactions, the mixtures were spotted on DE81 filter paper (Whatman), washed, dried and counted in a scintillation counter as described (Bryant et al, Biochemistry 22, 3537 (1983)).

Interaction with thioredoxin $K_{obs}$ (nM)

T7 DNA polymerase 50

Hybrid DNA polymerase 2000

Klenow fragment no interaction

EXAMPLE 3
Determination of Processivity of the DNA Polymerases

The effect of thioredoxin on the processivity of the hybrid DNA polymerase was determined as described (Tabor et al, JBC 262, 16212 (1987)) using m13mGP1-2 as the template and a 5'[$^{32}$P] labeled 25 nucleotide primer. A 100-fold excess of template over each enzyme was used. All reactions were carried out at 37° C. for 1 minute. Radioactively labeled fragments were analyzed by electrophoresis on an 8% polyacrylamide gel in 7 M urea. After electrophoresis the gel was dried and autoradiographed. The average processivity of each enzyme is summarized below, as determined by visual inspection of the autoradiograph.

| Average Processivity of DNA polymerases | | |
|---|---|---|
| Enzyme | − thioredoxin | + thioredoxin |
| Hybrid DNA polymerase | ~1 | ~30 |
| T7 DNA polymerase | ~1 | >300 |
| Klenow fragment | ~15 | ~15 |

EXAMPLE 4
Binding of Polymerase to Processivity Factor

Figure 2C:
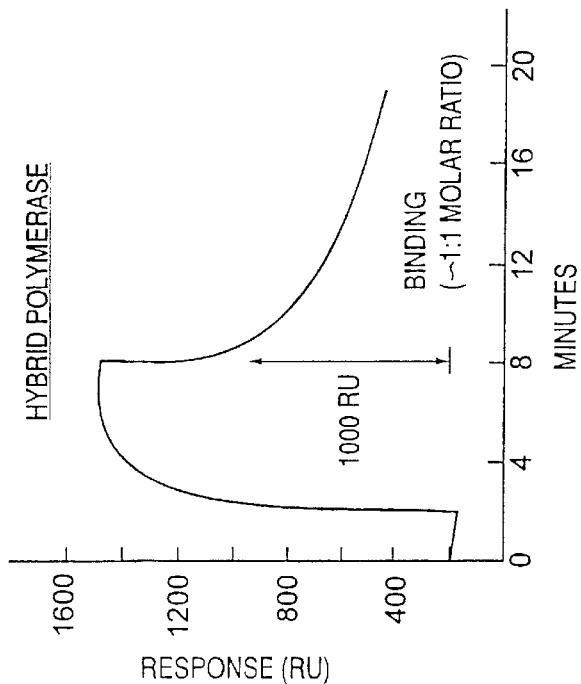
Figure 2B:
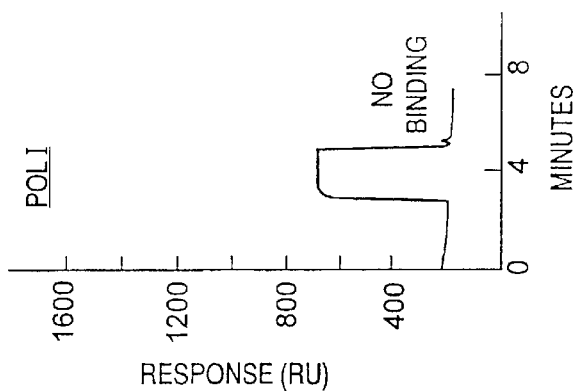
Figure 2A:
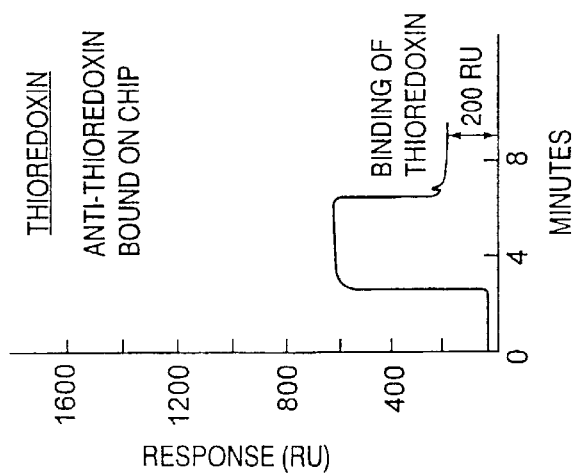

Referring to FIG. 2, the binding between The Klenow—T7 DNA polymerase hybrid and thioredoxin was directly demonstrated using Surface Plasmon Resonance Analysis (Biocor, Pharmacia). Monoclonal anti-thioredoxin antibodies were immobilized on the chip. In the absence of thioredoxin, neither Klenow fragment nor the hybrid DNA polymerase bound to the chip (not shown). When thioredoxin was passed over the chip, it bound stably to the antibodies. After binding of thioredoxin to the chip (FIG. 2A), the subsequent introduction of the hybrid DNA polymerase resulted in relatively tight binding of the hybrid DNA polymerase to the chip (FIG. 2C); the ratio of thioredoxin to the hybrid DNA polymerase is calculated to be one-to-one based on the relative Response Units. In contrast, Klenow fragment did not bind to the chip containing bound thioredoxin (FIG. 2B).

EXAMPLE 5
The Construction of a Klenow-TBD1 Hybrid DNA Polymerase

This example describes the insertion of the thioredoxin binding domain unique to T7 DNA polymerase (76 amino acid residues) into the homologous position in the large fragment of *E. coli* DNA polymerase I (Klenow fragment), without substituting any of the adjacent sequences. The gene encoding the 76 amino acid residues of T7 DNA polymerase has been spliced into the appropriate position of the gene for *E. coli* DNA polymerase I, resulting in the deletion of seven amino acid residues derived from *E. coli* DNA polymerase I. In contrast, in the previously described hybrid DNA polymerase (see Example 1), the smallest insert described was 127 amino acid residues from T7 DNA polymerase inserted in place of 60 amino acid residues of Klenow fragment.

This hybrid DNA polymerase (Klenow-TBD1) has much higher activity both in the absence and in the presence of thioredoxin than the previously described hybrid polymerase. Also, the Klenow-TBD1 hybrid DNA polymerase has dramatically higher processivity in the presence of thioredoxin than does Klenow fragment, the processivity is greater than 300 nucleotides, or greater than 20 times that of Klenow fragment. A further distinction between the Klenow-TBD1 DNA polymerase and the previously described hybrid polymerase is that it has a higher solubility.

Figure 4:
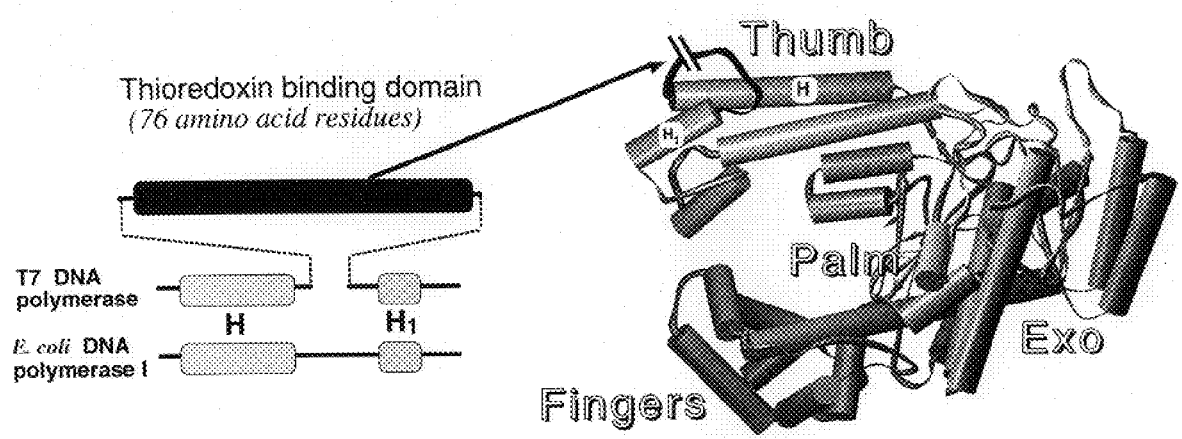
FIG. 4 is a diagrammatic representation of the Klenow fragment DNA polymerase with the thioredoxin binding domain of T7 DNA polymerase inserted at the homologous position, between the H and $H_1$ helices.

FIG. 4 shows a schematic drawing of the insertion of the thioredoxin binding domain from T7 DNA polymerase into the large fragment of *E. coli* DNA polymerase I (Klenow fragment). The gene producing this hybrid DNA polymerase was derived from the plasmid pCJ55 (Proc. Natl. Acad. Sci. 80, 1830 (1983)), that contains the gene for the Klenow fragment. The gene for the Klenow fragment was excised from pCJ55 by digestion with BamHI and HindIII, and the fragment was cloned between the BamHI to HindIII sites of pT7-5 (Current Protocols of Molec. Biol. 16.2.2 (1990), Ausubel et al., eds., Wiley Interscience, New York). This vector was digested with HindIII and AccI, and the ends were filled in and ligated. The resulting plasmid was partially digested with ClaI, then filled in and ligated. The resulting plasmid, pKLN0, had unique ClaI and BssHII sites positioned within the Klenow gene, that were used to clone the insert. This plasmid produces high levels of the Klenow fragment under the control of a T7 RNA polymerase promoter. The hybrid DNA polymerases were constructed using three PCR steps, by a modification of the procedure described in Biotechniques 8, 404 (1990). The first PCR reaction amplified the region of T7 gene 5 protein that encodes the thioredoxin binding domain, amino acid residues 258 to 333. The primers used for this reaction were chimeric, their 5' ends designed to contain sequences from the gene for *E. coli* DNA polymerase I that are adjacent to the position where the gene for the thioredoxin binding domain is to be inserted. The product of the first PCR reaction is then used in the second step as the primer for two PCR reactions using the gene for the Klenow fragment as a template; one reaction amplifies the sequences upstream of the site of the insert to the ClaI restriction site, while the second PCR reaction amplifies the region downstream of the site of the insert to the BssHII restriction site. In the third PCR reaction, the products of the two second PCR reactions were mixed and used both as template and primer for generating the whole ClaI-BssHII fragment with the desired insert. In each step the desired product of the PCR reaction was isolated out of an agarose gel after electrophoresis using a Qiagen gel extraction kit. The final PCR product was cloned into pKLN0 using the ClaI and BssHII sites. The sequence of this clone, that produces the protein Klenow-TBD1, is shown in FIG. 8 (SEQ. ID. NO:2).

EXAMPLE 6
The Overproduction and Purification of the Klenow-TBD1 DNA Polymerase The Klenow-TBD1 DNA polymerase was expressed in BL21(DE3)pLysS (Novagen). The cells were grown in LB media to O.D. 0.5 and induced with 0.5 mM IPTG for 2 hours. After harvesting, the cells were resuspended in 30 mM Tris-HCl, pH 7.5, 1 mM EDTA and 10% sucrose. The cells were lysed by incubating at 4° C. for 1 hour with 0.4 mg/ml lysozyme, then frozen and thawed three times. The cell debris was removed by centrifugation at 10,000 rpm for 30 min. The lysate was adjusted to 1 M ammonium sulfate and mixed with Phenyl Sepharose (Pharmacia) equilibrated with 30 mM Tris-HCl, pH 7.5, 1 mM DTT, 2 mM EDTA and 1 M ammonium sulfate. The resin was washed with the same buffer in the absence of ammonium sulfate; none of the Klenow-TBD1 DNA polymerase eluted in this step. The Klenow-TBD1 DNA polymerase was eluted with 20% acetonitrile. The eluted protein was dialyzed against 30 mM Tris-HCl, pH 7.5, 20 mM NaCl, 1 mM DTT, 2 mM EDTA and 10% glycerol (Buffer A). After dialysis, the Klenow-TBD1 DNA polymerase was further purified by FPLC Mono Q column chromatography (Pharmacia). The Klenow-TBD1 DNA polymerase was loaded onto the Mono Q in Buffer A, and then eluted with a linear gradient of 0 to 400 mM NaCl in Buffer A. The Klenow-TBD1 DNA polymerase eluted between 140–180 mM NaCl. The purified Klenow-TBD1 DNA polymerase was dialyzed against 20 mM $KPO_4$, pH 7.5, 0.1 mM DTT, 1 mM EDTA and 50% glycerol, and stored at $-20°$ C. After this procedure the purified Klenow-TBD1 DNA polymerase was greater than 80% pure as judged by SDS-PAGE, and the single prominent band migrated at a position corresponding to molecular weight 76,000.

EXAMPLE 7
Polymerase Assay of the Klenow-TBD1 DNA Polymerase

DNA polymerase activity of the Klenow-TBD1 DNA polymerase was compared to that of the Klenow fragment and the T7 gene 5 protein in the presence and absence of thioredoxin. DNA polymerase activity was measured by determining the incorporation of [$^{32}$P]dAMP into primed m13mGP1-2 (JBC 262, 16212 (1987); JBC 264, 6447 (189)). The template used was primed m13mGP1-2 annealed with a 20-mer oligonucleotide primer at a ten-fold excess over DNA polymerase. Reaction mixtures (50 $\mu$l) contained 40 mM Tris-HCl, pH 7.5, 10 mM $MgCl_2$, 5 mM DTT, 60 mM NaCl, 20 nM primed m13mGP1-2, 300 mM dCTP, dGTP, dTTP and [a-$^{32}$P] dATP (500 cpm/pmol), 2 nM DNA polymerase, and where present, 2 mM thioredoxin. The reactions were carried out at 37° C. for either 5 minutes (T7 gene 5 protein) or 15 minutes (Klenow fragment and Klenow-TBD1 DNA polymerase). Reactions were stopped by spotting the mixtures onto DE81 filter paper, the filters were washed in 0.3 M ammonium formate, pH 8, and counted using Optifluor O liquid scintillation fluor (Packard).

Typical results are presented below. One unit is defined as the incorporation of one pmol dNMP per minute.

| DNA Polymerase | Specific activity (units/$\mu$g DNA polymerase) | |
|---|---|---|
| | $-$ Thioredoxin | $+$ Thioredoxin |
| T7 gene 5 protein | <4 | 10,410 |
| Klenow | 2,110 | 2,180 |
| Klenow-TBD1 | 400 | 3,364 |

The DNA polymerase activity of the Klenow-TBD1 DNA polymerase was stimulated eight fold by the presence of thioredoxin; its activity in the presence of thioredoxin is greater than that of the Klenow fragment. Thioredoxin has no effect on the DNA polymerase activity of the Klenow fragment. The Klenow-TBD1 DNA polymerase is significantly more active in the absence of thioredoxin than is the T7 gene 5 protein.

EXAMPLE 8
Exonuclease Assay of the Klenow-TBD1 DNA Polymerase

Exonuclease activity was determined by a modification of a procedure previously described (JBC 264, 6447 (1989)). For the determination of double-stranded exonuclease activity, the template consisted of m13mGP-1-2 primed with a 22 mer oligonucleotide that was extended an average of 240 nucleotides in the presence of [a-$^{32}$P]dATP. The reaction mixture contained 550 nM dTTP, dGTP, dCTP and [a-$^{32}$P] dATP, 30 mM Tris-HCl, pH 7.5, 10 mM $MgCl_2$, 50 mM NaCl, 16 nM primed m13mGP-1-2, and 2 units of an exonuclease deficient mutant of Klenow fragment. The reaction was allowed to proceed for 10 minutes at 37° C., and then terminated by extraction with phenol. The extracted mixture was separated by gel chromatography on Sepharose CL6B (Pharmacia); the void volume contained the purified double-stranded primer-template at a specific activity of approximately 300,000 cpm/pmol nucleotides of double stranded DNA.

The exonuclease activity on double stranded DNA was assayed in a 50 ml reaction using 0.6 pmol (as nucleotides of double stranded DNA) of the labeled template, 40 mM Tris-HCl pH 7.5, 10 mM $MgCl_2$, 5 mM DTT, 50 mM NaCl, 3 nM of either Klenow fragment or Klenow-TBD1 DNA polymerase, or 6 nM T7 gene 5 protein. Where present, 8 mM of thioredoxin was added. Reactions were incubated at 37° C. for either 10 minutes (Klenow fragment and Klenow-TBD-1 DNA polymerase) or 1 minute (T7 gene 5 protein). Reactions were stopped with addition of 50 mM EDTA followed by TCA precipitation, using BSA as carrier. The supernatant was collected and counted using OptiFlour Gold liquid scintillation fluor (Packard).

For the determination of single-stranded exonuclease activity, uniformly labeled 900 bp DNA was synthesized using PCR in the presence of methyl-$^3$H dTTP (1 mCi/ml). The PCR product was purified using Geneclean kit (BIO 101). The resulting template was typically 0.3 nmol/ml nucleotides and 86,000 cpm/ml. Prior to use in the assays, the template was heat denatured by incubation at 100° C. for 5 minutes.

The exonuclease activity on single stranded DNA was assayed in a 50 ml reaction containing 0.15 nmol (as nucleotides) of the template, 40 mM Tris-HCl, pH 7.5, 10 mM $MgCl_2$, 5 mM DTT, 50 mM KCl, and either 30 mM of either Klenow fragment or Klenow-TBD1 DNA polymerase, or 3 nM T7 gene 5 protein. Where present, 2 mM thioredoxin was added. The reactions were incubated at 37° C. for either 5 minutes (Klenow fragment and the Klenow-TBD1 DNA polymerase) or 2 minutes (T7 gene 5 protein). Reactions were terminated and the products were precipitated with TCA and counted as described above for the double stranded exonuclease assay.

A typical comparison of the 3'-5' exonuclease activity on single stranded and double stranded DNA is shown below for the Klenow-TBD1 DNA polymerase, Klenow fragment and T7 gene 5 protein. Activities were calculated as the amount of dNMP released per mg protein per minute, and the data shown are relative values compared with that of the Klenow fragment. The levels of single-stranded and double stranded 3'-5' exonuclease activity of the Klenow-TBD1 DNA polymerase and the Klenow fragment are equivalent in the absence of thioredoxin, indicating that the thioredoxin binding domain insert does not impair proper folding of the enzyme in the exonuclease domain. Thioredoxin stimulates the double-stranded exonuclease activity of the Klenow-TBD1 DNA polymerase by approximately 40%; it has no effect on the double-stranded exonuclease activity by the Klenow fragment, nor on the single-stranded exonuclease activity by either enzyme.

| | Exonuclease activity (% of activity in Klenow fragment) | | | |
|---|---|---|---|---|
| | Double stranded DNA | | Single stranded DNA | |
| Enzyme | − Thioredoxin | + Thioredoxin | − Thioredoxin | + Thioredoxin |
| Klenow | [100] | [100] | [100] | [100] |
| Klenow-TBD1 | 100 | 150 | 140 | 140 |
| T7 gene 5 protein | 2130 | 32000 | 3930 | 3750 |

EXAMPLE 9

Figure 5:
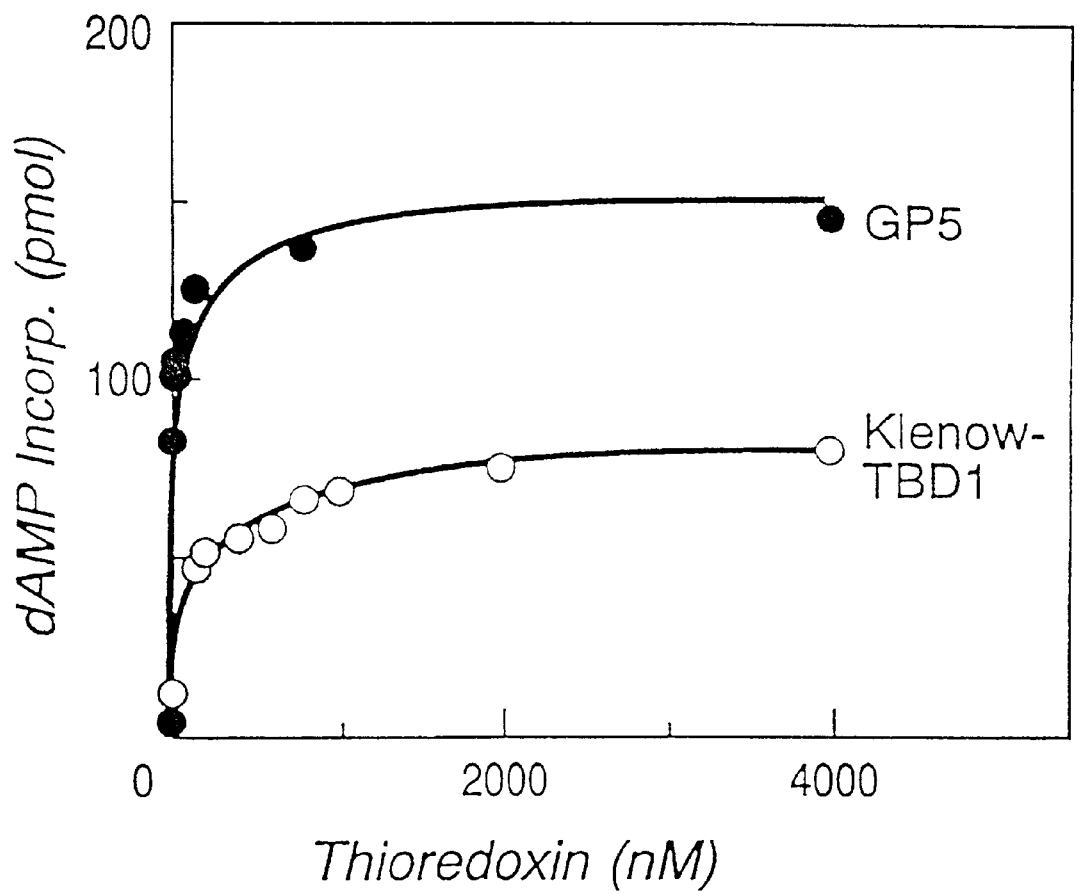
FIG. 5 shows the effect of increasing concentrations of thioredoxin on stimulation of DNA polymerase activity by Klenow-TBD1 and T7 gene 5 protein.

Measurement of Functional $K_D$ of Binding of Thioredoxin to Klenow-TBD1 DNA Polymerase Based on Polymerase Assay at Different Concentrations of Thioredoxin The affinity of thioredoxin for the Klenow-TBD1 hybrid DNA polymerase was determined as described (JBC 261, 15006 (1986)). Polymerase assays were carried out as in Example 7 except varying the concentration of thioredoxin. The stimulation of DNA polymerase activity by Klenow-TBD1 DNA polymerase or T7 gene 5 protein in the presence of an increasing concentration of thioredoxin is shown in FIG. 5. These data were used to generate a Scatchard plot, in which the amount of dTMP incorporated was plotted as a function of the amount of dTMP incorporated divided by the thioredoxin concentration (JBC 261, 15006 (1986)); in this plot the negative slope corresponds to the observed binding constant, $K_{obs}$ (i.e. the functional $K_D$). The $K_{obs}$ of the Klenow-TBD1 DNA polymerase for thioredoxin is 160 nM, approximately 10 fold higher than the value determined for the interaction of T7 gene 5 protein and thioredoxin (15 nM). The fact that the Klenow-TBD1 DNA polymerase binds thioredoxin less tightly than T7 gene 5 protein suggests that there may be other sites on T7 gene 5 protein that contribute to the binding to thioredoxin, albeit with a much more minor role than the interaction between the thioredoxin binding domain and thioredoxin.

EXAMPLE 10

Direct Measurement of the $K_D$ of Thioredoxin and the Klenow-TBD1 Hybrid DNA Polymerase by Surface Plasmon Resonance Analysis (Pharmacia BIAcore)

The binding of thioredoxin to the thioredoxin binding domain of the Klenow-TBD1 hybrid DNA polymerase can be measured directly by surface plasmon resonance (Anal. Biochem. 201, 197 (1992); Nature 361, 186 (1994)). In this experiment, monoclonal anti-thioredoxin antibodies are covalently complexed to a chip, and then thioredoxin is bound to the chip via its interaction with the antibodies. Interaction between thioredoxin and the Klenow-TBD1 hybrid DNA polymerase can then be determined directly by flowing the polymerase over the chip and measuring the change in surface plasmon resonance that results from binding.

Monoclonal anti-thioredoxin antibody (mAb) was covalently attached to the chip via amine groups on the protein and carboxy groups on the surface matrix of the chip; this chemistry was carried out using a kit purchased from Pharmacia. For kinetic measurements, the chip surface was activated with a 3.4 min pulse of 0.05 M NHS/0.2 M EDC at a flow rate of 5 ml/min, followed by a 2 minute pulse of the mAb, diluted to 50 mg/ml in 5 mM maleate, pH 7.0, followed by deactivation with a 3.4 minute pulse of 1 M ethanolamine. The flow buffer contained 10 mM HEPES, pH 7.5, 150 mM NaCl, 3.4 mM EDTA, 0.01% Tween 20, 0.1 mM DTT and 0.5% glycerol. The flow rate used in all the experiments was 5 ml/min. Kinetic data were generated using the BIAevaluation 2.1 software from Pharmacia. The chip surface was regenerated between injections of the Klenow-TBD1 DNA polymerase by a 2 minute pulse of 10 mM glycine, pH 9.5, that removed the Klenow-TBD1 DNA polymerase from the chip but not the thioredoxin.

An example of a typical experiment is shown in FIGS. 6(A–C). In panel 6A, thioredoxin was passed over the chip containing bound antibody, and one can see that it stably binds to the surface, resulting in an increase in the baseline by 250 resonance units (RU). The binding of thioredoxin to the antibody is extremely stable and decays at a rate that is negligible compared to the time required to carry out the binding experiments between the Klenow-TBD1 DNA polymerase and thioredoxin. In panel 6B, Klenow fragment is passed over the chip; no additional binding is observed. In panel 6C, the Klenow-TBD1 DNA polymerase is passed over the chip; immediately at the end of the injection (i.e., once the increase in the resonance units due to the bulk refractive index decays), there is an increase of 1500 RU as a result of the DNA polymerase binding to thioredoxin. The increase in resonance units is proportional to the change in the refractive index (BioTechniques 11, 620 (1991)), and therefore to the change in the mass bound to the chip. Since the mass ratio between the Klenow-TBD1 DNA polymerase and thioredoxin is 6.7, the increase observed here corresponds to 90% of the thioredoxin on the chip surface being bound by a DNA polymerase molecule. Increasing the concentration of the Klenow-TBD1 DNA polymerase being injected, or increasing the injection time to ensure that equilibrium has been reached, did not result in an increase of resonance units above 1600, showing that the complex formed is a 1:1 ratio of thioredoxin to the Klenow-TBD1 DNA polymerase.

The association and dissociation rate constants ($k_a$ and $k_d$) were determined directly from the binding curves at five concentrations of the Klenow-TBD1 DNA polymerase, as shown in FIG. 7. The association rate constant was determined from a plot of $k_s$ derived from the association part of each curve, versus the concentration of the Klenow-TBD1 DNA polymerase; the slope of this plot is equal to $k_a$. The dissociation rate constant was taken as the average of the values derived from the dissociation part of each curve. The equilibrium rate constant, $K_d$, is the ratio between $k_d$ and $k_a$; the value obtained was 9.5 nM. The difference between the value obtained here and the observed equilibrium constant measured in the previous example could be explained by the different systems used by the two procedures. The thioredoxin in this example was immobilized on the surface, versus in the previous example it was free in solution. In addition, whereas the value obtained here is a direct physical measurement of binding, the values obtained in the synthesis assay are derived indirectly via measurements of DNA synthesis, where other factors may influence the apparent binding constant.

EXAMPLE 11

Measurement of the Processivity of the Klenow-TBD1 Hybrid DNA Polymerase

Processivity was measured by a modification of the procedure previously described (JBC 262, 16212 (1987)). A 22-mer oligonucleotide was $^{32}$P-labeled at its 5' end, and annealed to the 10,000 nucleotide, single-stranded circular M13 mGP1-2 DNA template. The annealed primer-template was purified by gel filtration on a Sepharose CL6B column; the specific activity was ~$10^7$ cpm/pmol. The reaction mixture (10 μl) contained 40 mM Tris-HCl pH 7.5, 50 mM NaCl, 5 mM DTT, 10 mM MgCl$_2$, 0.3 mM dNTPs, and 1.4 nM of $^{32}$P-labeled primer-template molecules. Indicated DNA polymerases were added at a final concentration of either 0.14 nM or 0.014 nM, corresponding to a primer-template to DNA polymerase ratio of 10:1 or 100:1, respectively. Where present, the thioredoxin concentration was 20 μM. The reaction mixtures were preincubated at 37° C. and then the reactions were initiated by the addition of DNA polymerase. The reactions were carried out at 37° C. for one minute, and then terminated by the addition of 10 ml of 95% formamide and 25 mM EDTA. DNA products were separated by denaturing acrylamide gel electrophoresis. After electrophoresis the gels were dried and autoradiographed to determine the size of the extended $^{32}$P-labeled primers.

Under the conditions described above, the average processivity of the Klenow fragment is about 15 nucleotides in the presence or absence of thioredoxin. In contrast, the Klenow-TBD1 hybrid DNA polymerase has an average processivity of about 10 nucleotides in the absence of thioredoxin, and greater than 300 nucleotides in the presence of thioredoxin.

EXAMPLE 12
Hybrid Tth DNA Polymerase

*Thermus thermophilus* DNA polymerase (Tth DNA polymerase) is a thermophilic DNA polymerase that is 87% homologous to Taq DNA polymerase (J. Ferment. Bioeng. 76, 265 (1993)). In contrast to Taq DNA polymerase, Tth DNA polymerase is a very good reverse transcriptase; it is more than one hundred fold more efficient as a reverse transcriptase than Taq DNA polymerase (Biochem. 30, 7661 (1991)). As a consequence, Tth DNA polymerase has become widely used for the PCR of RNA (for example, see Perkin Elmer RNA PCR Kit, Part No. N808-0069). A hybrid Tth DNA polymerase with improved processivity as a reverse transcriptase can be constructed by placing the thioredoxin binding domain of T7 DNA polymerase into Tth DNA polymerase, in order to increase its processivity on RNA templates in the presence of thioredoxin. This should improve the ability of this enzyme to synthesize full-length cDNAs, which is important for the construction of cDNA libraries of high quality, and for quantitative PCR of mRNA.

Using techniques similar to those utilized to construct the other chimeric polymerases of the invention, the thioredoxin binding domain of T7 DNA polymerase can be inserted in place of residues 477 to 483 of the Tth DNA polymerase to construct one such hybrid Tth DNA polymerase.

EXAMPLE 13
Use of Thermophilic Thiorodoxin

A thermophilic thioredoxin could be utilized to confer high processivity to a thermophilic DNA polymerase containing a thioredoxin binding domain. Such thermophilic thiorodoxin would be useful when the thioredoxin binding domain from T7 DNA polymerase is inserted into Taq DNA polymerase, in order to improve the processivity of Taq DNA polymerase in the presence of thioredoxin. It is important that the thioredoxin is heat stable so that the Taq DNA polymerase-thioredoxin complex can be used in PCR applications. Wild-type thioredoxin has been shown to denature at 86° C. (JBC 271, 5059 (1996)). However, a single mutation in thioredoxin, D26A (aspartic acid 26 to alanine), increases the melting temperature at least 10° C., to greater than 96° C. (JBC 271, 5059 (1996)). This residue is buried in the interior of thioredoxin and thus unlikely to effect the interaction of thioredoxin with the thioredoxin binding domain. Mutant thioredoxin with enhanced thermal stability, such as described above, or naturally occurring thermophilic thioredoxin can be used instead of wild-type thioredoxin with chimeric thermophilic DNA polymerases containing the thioredoxin binding domain, in order to potentially stabilize the complexes at high temperatures. Those of ordinary skill in the art utilizing known techniques could construct other thermophilic thioredoxin mutants and other thermophilic processivity factors.

Chimeric Polymerases

The above experiments indicated that we have identified the region of T7 DNA polymerase that binds thioredoxin. Transferring that region into *E. coli* DNA polymerase I results in a hybrid DNA polymerase whose processivity is dramatically increased by the presence of thioredoxin. It is thus now possible that to make similar substitutions into Taq DNA polymerase or other polymerases to increase their processivity. For example, the processivity factor binding domain can be inserted in place of residues 475–481 of Taq DNA polymerase. This is significant for use of these enzymes for DNA sequencing through difficult templates, and for long PCR.

One other Pol I-type DNA polymerase has a unique region at the position of the unique sequence in T7 DNA polymerase. That is the DNA polymerase from bacteriophage SP01. It is known that SP01 DNA polymerase is highly processive (Yehle and Ganesau, JBC 248, 7456 (1973)). This region (between Helices H and H1) in SP01 may also be serving to bind a processivity factor from its host, *B. subtilis*, or may be a processivity factor itself. Such a region can also be used as described in this application, in place of the region in T7 DNA polymerase.

Trans Acting Domains

T5 DNA polymerase is a pol I-type DNA polymerase. It is highly processive without any additional processivity factor. Compared with other PolI-type DNA polymerases, it has an insert of about 15,000 daltons at the C terminus of the molecule (Braithwaite and Ito, supra). In the structure of *E. coli* DNA polymerase I the C terminus is near the site corresponding to the thioredoxin-binding domain in T7. Thus this domain at the end of T5 DNA polymerase could serve the role that thioredoxin serves in T7 DNA polymerase, namely, acting as a clamp to hold the polymerase on the primer-template. Thus, this region could be expressed in trans to increase the processivity of T5 DNA polymerase, or other DNA polymerases. Alternatively, it can be introduced into another DNA polymerase to increase the processivity of the polymerase.

DNA Polymerase Inserts

Applicant has shown that inserts can be made into a DNA polymerase, and in particular between helices H and H1 of a PolI-type DNA polymerase. This indicates that it is now possible to produce chimeric DNA polymerases having inserts in such a region having various activities. For example, other enzyme activities can be introduced, e.g., those useful in PCR or in DNA sequencing, such as pyrophosphatase, alkaline phosphatase, exonuclease, methylases, restriction enzymes and the like. Such enzymes will enhance utility of the DNA polymerase in such methods.

Other embodiments are within the following claims.

We claim:

1. A chimeric DNA polymerase having a DNA polymerase domain and a processivity factor binding domain not naturally associated with said DNA polymerase domain, wherein said processivity factor binding domain binds thioredoxin.

2. A chimeric DNA polymerase having a DNA polymerase domain and a processivity factor binding domain not naturally associated with said DNA polymerase domain, wherein said processivity factor binding domain consists essentially of amino acids 236 to 363 from T7 gene 5 protein.

3. A chimeric DNA polymerase having a DNA polymerase domain and a processivity factor binding domain not naturally associated with said DNA polymerase domain, wherein said polymerase consists essentially of a wild-type DNA polymerase having substituted in a region of the wild-type DNA polymerase corresponding to amino acids 549 to 609 of Klenow fragment of DNA polymerase I, a processivity factor binding domain that corresponds essentially to amino acids 236 to 363 of T7 gene 5 protein.

4. A chimeric DNA polymerase having a DNA polymerase domain and a processivity factor binding domain not naturally associated with said DNA polymerase domain, wherein the processivity factor binding domain consists essentially of amino acid residues 258 to 333 of T7 DNA polymerase.

5. The chimeric DNA polymerase of claim 4 wherein the processivity factor binding domain is inserted in place of residues 571 to 577 of E. coli DNA polymerase I.

6. The chimeric DNA polymerase of claim 4 wherein the processivity factor binding domain is inserted in place of residues 475 to 481 of Taq DNA polymerase.

7. The chimeric DNA polymerase of claim 4 wherein the processivity factor binding domain is inserted in place of residues 477 to 483 of Tth DNA polymerase.

8. A processivity factor modified to increase its heat stability.

9. The processivity factor of claim 8, wherein said factor is thioredoxin and said modification is the replacement of aspartic acid 26 with alanine.

10. The processivity factor of claim 8, wherein said factor is thioredoxin.

11. The processivity factor of claim 10, wherein said factor is thioredoxin and said modification is the replacement of aspartic acid 26 with alanine.

12. A chimeric DNA polymerase having a DNA polymerase domain and a processivity factor binding domain not naturally associated with said DNA polymerase domain, wherein said processivity factor binding domain is inserted in place of residues 571 to 577 of E. coli DNA polymerase I.

13. A chimeric DNA polymerase having a DNA polymerase domain and a processivity factor binding domain not naturally associated with said DNA polymerase domain, wherein said processivity factor binding domain is inserted in place of residues 475 to 481 of Taq DNA polymerase.

14. A chimeric DNA polymerase having a DNA polymerase domain and a processivity factor binding domain not naturally associated with said DNA polymerase domain, wherein said processivity factor binding domain is inserted in place of residues 477 to 483 of Tth DNA polymerase.

* * * * *